United States Patent
Rotvold

(10) Patent No.: US 10,441,360 B2
(45) Date of Patent: Oct. 15, 2019

(54) SYSTEM FOR PRECISION GUIDANCE OF SURGICAL PROCEDURES ON A PATIENT

(71) Applicant: METRONOR AS, Nesbru (NO)

(72) Inventor: Oyvind Rotvold, Hvalstad (NO)

(73) Assignee: Metronor AS, Nesbru (NO)

( * ) Notice: Subject to any disclaimer, the term of this patent is extended or adjusted under 35 U.S.C. 154(b) by 656 days.

(21) Appl. No.: 14/710,869

(22) Filed: May 13, 2015

(65) Prior Publication Data

US 2015/0327946 A1 Nov. 19, 2015

(30) Foreign Application Priority Data

May 13, 2014 (EP) .................................... 14168083

(51) Int. Cl.
*A61B 34/00* (2016.01)
*A61B 34/10* (2016.01)
(Continued)

(52) U.S. Cl.
CPC .............. *A61B 34/10* (2016.02); *A61B 34/20* (2016.02); *A61B 2034/105* (2016.02);
(Continued)

(58) Field of Classification Search
CPC .............................. A61B 6/5247; A61B 90/10
See application file for complete search history.

(56) References Cited

U.S. PATENT DOCUMENTS 6,224,227 B1 * 5/2001 Klootz ................ F21V 33/0052
  348/370
6,405,072 B1 * 6/2002 Cosman ............... A61B 6/5247
  600/426
(Continued)

FOREIGN PATENT DOCUMENTS

DE 19649399 A1 6/1998
EP 607303 B1 9/1996
(Continued)

OTHER PUBLICATIONS

European Patent Application No. 14168083 filed May 13, 2014 titled *A system for precision guidance of surgical procedures on a patient*, 20 pages.
(Continued)

*Primary Examiner* — Joseph M Santos Rodriguez
(74) *Attorney, Agent, or Firm* — Kilpatrick Townsend & Stockton LLP

(57) ABSTRACT

A system for precision guidance of surgical procedures on a patient is disclosed. Aspects of the system may include: a three-dimensional digital representation of a pre-procedural geometry of a relevant part of the patient, a three-dimensional digital representation of an intended post-procedural geometry of the relevant part of the patient including any implant or other structures intended to be attached to the patient, and a movable electro-optical (EO) camera mounted in a known position and orientation relative to a surgeon, such as a head mount. Further aspects of the system may include a first carrier comprising at least 3 targets to be observed by the EO camera, wherein the first carrier may be mounted in a known first position and first orientation relative to the relevant part of the patient, and a second carrier comprising at least 3 targets to be observed by the EO camera, wherein the second carrier may be mounted in a known second position and second orientation relative to an implant or surgical instrument. Embodiments of the system may include a computer for calculating, based on observations from the EO camera, relative positions of the first and second carriers and of the EO camera. Embodiments of the system may also include software, residing on the computer, configured to calculate a relevant projection of a digital representation of the patient to be displayed in order for the displayed projection to match with the surgeon's current physical view of the patient.

9 Claims, 2 Drawing Sheets

(51) Int. Cl.
*A61B 34/20* (2016.01)
*A61B 90/50* (2016.01)
*A61B 90/00* (2016.01)

(52) U.S. Cl.
CPC ............... *A61B 2034/2055* (2016.02); *A61B 2034/2057* (2016.02); *A61B 2090/364* (2016.02); *A61B 2090/368* (2016.02); *A61B 2090/502* (2016.02)

(56) References Cited

U.S. PATENT DOCUMENTS

| | | | | |
|---|---|---|---|---|
| 6,920,347 | B2* | 7/2005 | Simon | A61B 6/12 128/898 |
| 7,774,044 | B2 | 8/2010 | Sauer et al. | |
| 2008/0135733 | A1* | 6/2008 | Feilkas | A61B 90/36 250/208.1 |
| 2013/0267838 | A1 | 10/2013 | Fronk et al. | |

FOREIGN PATENT DOCUMENTS

| | | | |
|---|---|---|---|
| EP | 1712193 | A1 | 10/2006 |
| EP | 2544039 | A1 | 1/2013 |

OTHER PUBLICATIONS

Extended European Search Report and Written Opinion dated Nov. 12, 2014 for European Patent Application No. 14168083.5 filed May 13, 2014, all pages.
First Chinese Examination Report dated Nov. 5, 2018 for Chinese Patent Application No. 201510234408.X filed May 13, 2014, all pages.

* cited by examiner

SYSTEM FOR PRECISION GUIDANCE OF SURGICAL PROCEDURES ON A PATIENT

CROSS-REFERENCES TO RELATED APPLICATIONS

This application claims priority to EPO 14168083 filed May 13, 2014, titled, "A SYSTEM FOR PRECISION GUIDANCE OF SURGICAL PROCEDURES ON A PATIENT," the contents of which are incorporated by reference herein.

BACKGROUND OF THE INVENTION

This application is directed to systems for guidance of surgical procedures on a patient. Such systems may be used, for example, in knee or hip replacement surgeries.

SUMMARY OF THE INVENTION

The embodiments of the invention disclose systems for guidance of surgical procedures on a patient.

In an embodiment, a system comprises a computer comprising a processor and a memory, a display device that is communicatively linked with the computer, and a movable electro-optical camera that can be mounted in a known first position and known first orientation. The embodiment further comprises a three-dimensional digital representation of a pre-procedural geometry of a relevant part of the patient, and a three-dimensional digital representation of an intended post-procedural geometry of the relevant part of the patient that includes a representation of a surgical implant that is to be attached to the patient during the surgical procedure. The embodiment further comprises first and second carriers, each of which comprises at least 3 respective targets that are observable by the camera. The first carrier can be mounted in a known second position and a known second orientation relative to the relevant part of the patient. The second carrier can be mounted in a known third position and a known third orientation relative to either of the surgical implant or a surgical instrument. The embodiment further comprises software residing on the computer memory that contains instructions which, when executed, cause the computer to calculate and display a projection of a digital representation of the relevant part of the patient onto the display device in order for the displayed projection to match a current physical view of the patient by the surgeon.

Additional and/or alternative embodiments may include any combination of the following aspects. The three-dimensional digital representation of a pre-procedural geometry and the three-dimensional digital representation of the intended post-procedural geometry may be combined into a single digital representation.

The camera may be capable of capturing an image of the targets on the first carrier and the targets on the second carrier at the same instant. The camera may be a digital camera calibrated to measure spatial directions to the targets of the first and second carriers in space.

The software may cause the computer to calculate an image showing how one of the first and second carriers should be moved relative to the patient or relative to the remaining another carrier to reach a desired relative position and orientation, and to display the image onto the display device.

The system may comprise a third carrier comprising at least 3 targets observable by the camera, wherein the third carrier is mountable in a fourth position and fourth orientation relative to any one of: (i) a part of the patient, (ii) the surgical implant, or (iii) the surgical instrument.

The targets of either the first or second carriers may comprise active light emitting elements. The targets of the first carrier may form a first pattern that is distinct from a second pattern formed by the targets of the second carrier.

DESCRIPTION OF THE DRAWINGS

A further understanding of the nature and advantages of various embodiments may be realized by reference to the appended figures. The figures only illustrate exemplary embodiments to help understand the disclosure give in the Detailed Description of the Invention, and are not intended to illustrate limitations of the embodiments. In the appended figures, similar components or features may have the same reference label. Further, various components of the same type may be distinguished by following the reference label with a dash and a second label that distinguishes among similar components. When only the first reference label is used in the specification, the description is applicable to any one of the similar components having the same first reference label irrespective of the second reference label.

DETAILED DESCRIPTION OF THE INVENTION

I. Introduction

Figure 1:
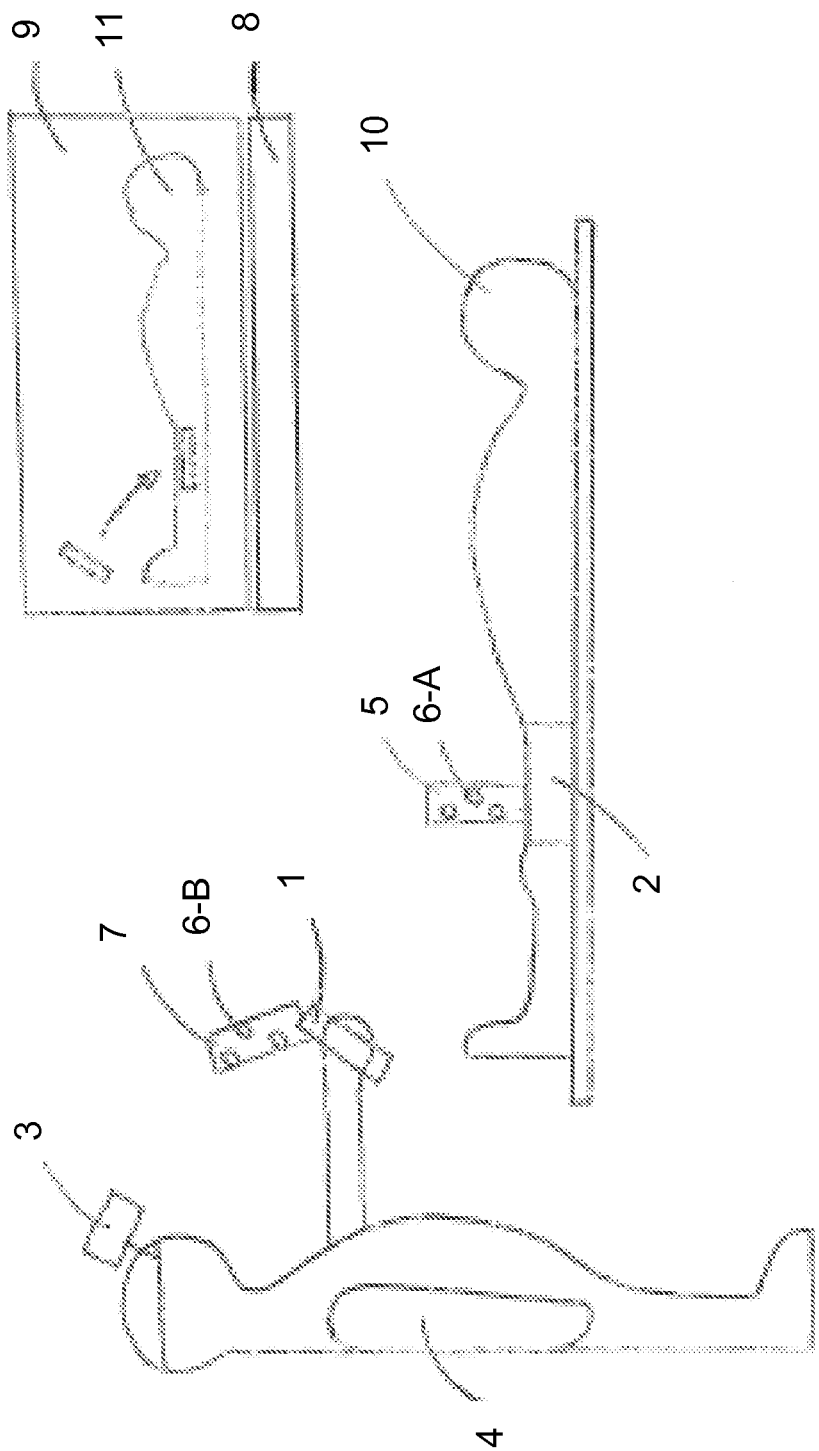
FIG. 1 shows a configuration of a computer guidance system for a surgical procedure, according to an embodiment.

While there is agreement that computer guidance systems have the potential to both lower the risk and improve the outcome of many surgical procedures such as Total Knee or Hip Arthroplasty, or Spinal Fusion procedures, the adaptation of such systems remains low. For example, several systems are commercially available that may guide a surgeon in positioning an implant—such as a hip implant—precisely by simultaneously tracking several objects such as the patient, the implant and other instruments. However, to be a practical solution, the guidance apparatus should not obstruct or obscure the surgical teams' work, nor require the surgical team to work in an unfamiliar way. For example, the system should allow a for a clear view to the wound. Also, navigation targets attached to the patient, the implant, and other instruments should also not interfere with the surgeon's work, but should provide reliable positioning guidance throughout the procedure.

Systems for measuring the position and orientation in space of a pattern of targets, e.g. a pattern comprising at least 3 targets in known positions relative to each other, are described for example in EP 607 303 B1, the contents of which are incorporated herein by reference herein.

It follows that the position and orientation of any object stiffly connected with the pattern of targets can therefore also be measured. Such an object might be a measurement probe, or it could be a part of an assembly one wishes to position into a specific placement—such as an implant—or an object one wishes to track through time and space—such as a bone structure undergoing surgery.

It is further known, e.g., from EP 607 303 B1, that if the relative positions of the individual targets of a pattern of at least 3 targets is known—and certain constraints are placed on the target pattern—then the position and orientation in three-dimensional space of this pattern of targets relative to a camera can be determined from the two-dimensional picture of the targets taken by the camera.

If a picture is taken that contains two or more non-identical known patterns of targets, it therefore follows that it is possible to determine the spatial position and orientation of each of these patterns of targets relative to the camera. This enables a system derived from the teachings of EP 607 303 B1 to measure the position and orientation of several objects—for example, the femur and the implant in the case of a Total Knee Arthroplasty—at the same time.

If the known patterns of targets are identical, their spatial position and orientation can still be determined provided (1) an initial position for each is known, and (2) subsequent movement between pictures is small enough to track each pattern through time, and (3) at no point in time are the two patterns overlapping or closer to overlapping than the movement since the previous picture.

Alternative systems with similar capabilities are presented e.g. in EP 1 712 193 A1 and in DE 196 49 399 A1, both of which are incorporated by reference herein. Both of these systems are also able to determine the position and orientation of multiple objects, and like EP 607 303 B1, both require a stationary camera.

All measurements made with a system such as those described in EP 607 303 B1, EP 1 712 193 A1 and DE 196 49 399 A1 are made in a reference frame tied to the camera, typically through an initial process of using a measurement probe and touching a number of reference features. This is stated explicitly in DE 196 49 399 A1, and is implicit in the description of EP 1 712 193 A1 as one would otherwise need to establish some other reference frame to relate the measurements to.

Additionally, the IR sensors taught in EP 1 712 193 A1 and DE 196 49 399 A1 are not capturing instantaneous scenes, but are—admittedly quickly—measuring point by point and cannot measure two or more points simultaneously. This reduces accuracy slightly, as the different targets are captured at slightly different points in time. This is not critical, as the movements involved are relatively small. It does, however, require that the camera be stationary during measurement, as the measurement accuracy would otherwise be ruined due to the long distance between the sensor and the targets. In a camera-fixed coordinate system, a small angular movement of the camera will cause a large shift in the position of a target, and targets observed at even slightly different times will have large relative deviations—worse the further from the camera they are. Therefore, it is essential for these known systems that the camera is held stationary, as the relationship with the references is otherwise lost.

Such systems are therefore ill suited for the practical implant placement task. During this type of surgery involving large forces and extensive mechanical forming of bone structure, it is impractical to keep the patient still, and also impractical to hold the camera still as it would either lose line-of-sight to the wound during surgery, or get in the way of the medical staff.

In some embodiments, planning is integrated with the guidance system so that the surgeon receives easy-to-relate-to and intuitive guidance on how (e.g. move the implant) to achieve the planned position during the procedure itself. At the same time, the guidance information should be provided in such a way so as to not take the surgeon's focus away from the wound, nor cause additional fatigue (e.g. when using surgical loupes).

Several such planning tools are commercially available, including solutions marketed by, e.g., Medtronic and Brainlab, and several may be integrated with guidance systems. However, they all rely on the surgeon to interpret two-dimensional representations mostly presented in a fashion similar to conventional X-ray images, or to manually select the relevant views and projections during the procedure. This adds time, may increase the risk of misinterpretations and removes focus from the procedure itself.

A number of existing solutions provide guidance based on generic patient models—either a completely generic model, or a patient approximation selected from a library of patient types based on gender, size, age, shape or other selection characteristics. While this is useful for procedural guidance (e.g. in a teaching situation), it is clearly less useful if guidance to improve the precision of the procedure is the goal. In some embodiments, to achieve sub-millimeter guidance precision, the model used for planning and guidance should is a precision representation of the individual patient. Technologies exist to extract such computer representations, e.g., from CT scans.

The use of a guidance system also should not add significantly to the duration of the procedure, both for financial reasons and to avoid increasing the risk of infections. Setup and alignment times are short and the use of the system is simple and intuitive to be perceived as an efficient aid by the surgeon.

It is important that the positioning of system components are not obstructing or hindering the established work-flow, but allows the surgical team to carry out the procedure using familiar methods and employing established skills.

In addition, the guidance equipment desirably should be cost-efficient to purchase and robust and reliable to avoid failures during the procedure. The system components that come in contact with the patient should be disposable or suitable for sterilizing.

An efficient solution for surgical guidance would preferably fulfill a number of criteria, among them are the following: (a) the ability to obtain an accurate three-dimensional representation of the individual patient, (b) the ability to use this representation for surgical planning purposes and to create a modified model showing the intended post-procedure geometry, (c) the ability to track multiple objects (patient, instruments, implants, etc.) simultaneously, (d) the ability to use a navigation unit—such as a camera—that can be moved during the procedure so as to not obscure or unduly restrict surgical team movement, and (e) the ability to track the movement of the surgeon relative to the patient in order to automatically display graphical guidance information in the relevant projection.

II. Guidance System

The object of the present invention is to provide an integrated system that provides to surgeons precise and intuitive spatial measurement data needed for precision guidance of surgical procedures without obstructing or obscuring the wound. This object can be achieved by a system such as presented in the Summary of the Invention, and as described herein. Various advantageous embodiments of the inventive system are also described.

Embodiments of the inventive system permit efficient and precise measurements of two or more moving or movable objects relative to each other, particularly of a surgical implant relative to the element in a patient to which the surgical implant is to be fixed. Embodiments of the present invention provide a set of targets following the patient, an independent set of targets following the surgical implant, and a measurement camera viewing these targets. A set of targets may be placed on a common structure, called a carrier. Further, each set of targets, and/or the carriers comprising targets, as well as the camera may move or be moved independently relative to each other during measurement, thus providing the necessary flexibility to be a practical solution to the problems discussed above.

In some embodiments the camera is configured to be mounted on the head of a surgeon performing the procedure. By mounting the camera on the surgeon's head, two benefits are achieved over traditional overhead or ceiling mounts. First, the camera will always have an unimpeded view of the wound as the surgeon performs the procedure. Second, the camera will never be in the way of the surgeon's work, nor will the surgeon have to make allowances in his work to ensure that the camera does not lose view of the scene during the procedure.

To support a head-mount, it is necessary for the camera to be small, light-weight and well balanced. A single-camera approach like that taught in EP 607 303 B1 is therefore advantageous over approaches using multiple cameras or sensing arrays. Systems based on EP 607 303 B1 have been commercially available for many years and have proven accuracy more than sufficient to support surgical guidance applications.

Advanced imaging techniques like CT, MRI and PET have enabled detailed mapping of patients' interior geometry. These techniques typically produce in the first instance a series of planar sections through the patient. Techniques also exist and are constantly improved to generate 3D models from these series of sections. A number of challenges have to be addressed; it is for example not always easy to precisely determine the transition from bone to surrounding material. At present, this technology has been demonstrated to yield patient-specific models of a quality useful in surgical procedures.

Once a patient-specific 3D model is available, the surgeon can avail himself of tools similar to the CAD tools of industry, where the intended changes can be designed, reviewed, refined and analyzed on a computer. A number of solutions exist for planning surgical procedures on computer, although not all can relate to patient-specific models.

Planning is most beneficial when the plan can be used as a basis for guidance during the procedure. Embodiments of the surgical guidance system therefore (a) have access to the patient-specific model or representation, (b) also have access to the planned changes to the patient-specific geometry, such as the precise areas to be removed, the precise position and orientation intended for any implants to be inserted and so on.

An initial step in the surgical procedure will therefore be to register the patient in such a way that the guidance system can align the relevant parts of the physical patient with the digital representation. This is achieved in various embodiments by using a hand-held carrier with targets, where the carrier also has a touch point that can be used to indicate salient points on the patient that are also known in the digital representation. Thereafter, another carrier with targets is attached fixedly to the relevant part of the patient, thus enabling the system to continuously align the digital representation with the current position and orientation of the physical patient.

The invention applies the principle that knowing the position and orientation of the two or more patterns of targets at given simultaneous instances in time, it is possible to calculate the relative position and orientation of the two or more targets to each other at the same instances, as well as the observation that this will hold true also if the camera is moved relative to the two patterns of targets, thus enabling a measurement system where the camera can be moved independently from any one or all of the patterns of targets and still provide measurements of their relative position and orientation to each other. From the camera observations, the relative positions and orientations of all three units—the camera and the two carriers—may be calculated.

During the remainder of the procedure, it is therefore possible to determine where the patient is relative to the surgeon—who is wearing the head-mounted camera. Therefore, it is also possible to display the representation of the patient in the same orientation relative to the surgeon as the physical patient. This can serve to lower surgeon work-load and make the guidance more intuitive.

FIG. 1 shows schematically an application of an embodiment of the system during a surgical procedure. A patient 10 has a first carrier 5 with targets 6-A attached to a relevant part 2 of the patient 10 for tracking the part's current position. A surgeon 4 wearing a movable head-mounted camera 3 is placing an implant 1 with an attached second carrier 7, with targets 6-B, into the patient at the planned position. The display device 9 shows the digital representation 11 of the patient 10, calculated by a computer 8 based on images generated by the camera 3.

As an example, during hip replacement surgery, an implant 1 needs to be placed precisely relative to an undamaged part of the femur bone 2. The intended position has been planned beforehand. Due to the nature of the procedure, it is impractical and/or impossible to keep the femur bone 2 still and it is further impractical to maintain a suitable, stable camera position as the camera will get in the way of the surgeon. Embodiments of the present invention provide for a movable camera 3, for example head-mounted worn by the surgeon 4, to provide a clear view into the wound area without obstructing the surgeon's view or movement. A carrier 5 with three targets 6-A is mounted to the undamaged part of the femur bone 2 providing a continuously updated reference locked to the femur bone 2. Another carrier 7 with three targets 6-B is mounted to the implant 1, providing continuous updates on the relative position of the implant 1 relative to the undamaged part of the femur bone 2. In some embodiments, the arrangement or pattern of the targets 6-B differs from that of the targets 6-A so that two targets can be distinguished. The computer 8 receives images from the camera 3 and calculates the relative positions and orientations of the carriers 5 and 7 with the respective targets 6-A and 6-B. This enables comparison between the desired and current position and orientation of the implant 1 relative to the femur bone 2 as long as the carriers 5 and 7 with respective targets 6-A and 6-B are within the field of view of the camera 3. This enables the system to compute and display to the surgeon, on the display device 9, how to move the implant 1 relative to the femur bone 2 in order to achieve the desired position, while always matching the displayed orientation with the actual patient position from the surgeon's point-of-view.

The surgeon 4, the patient 10 and the implant 1 may move freely relative to each other during the measurement. The camera 3 captures images of the carriers 5 and 7 with respective targets 6-A and 6-B essentially simultaneously, or—depending on the required accuracy—closely enough in time to calculate a consistent set of relative positions and orientations for the carriers 5 and 7. The system comprises a display device 9, either directly connected to the computer 8 itself, or remotely located in a suitable location for viewing during the procedure such as on a wall. Embodiments of such display devices include CRT monitors, and LCD or plasma display screens. The computer and the display device are communicatively linked, which may be by a wired or a wireless connection. In other embodiments the display device 9 may be a semi-transparent display visor worn by the surgeon. The display device 9 may be capable of showing how the implant 1 should be moved relative to the patient 10 to reach the desired relative position.

III. Computer System

Figure 2:
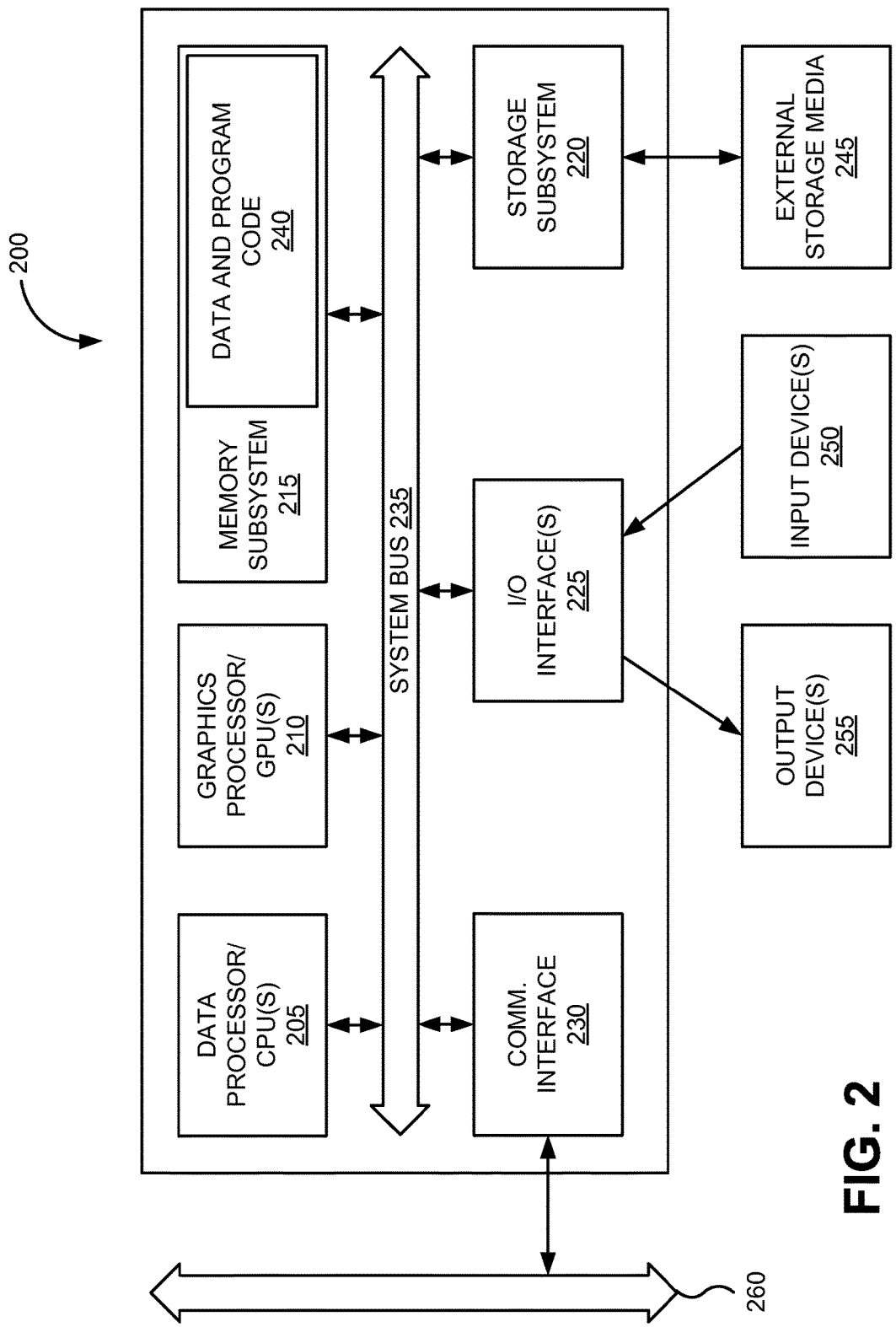
FIG. 2 is computer system, according to an embodiment.

FIG. 2 is a block diagram of computer system 200 such as may be used as part of the guidance system of surgical procedures disclosed above. FIG. 2 is merely illustrative. In some embodiments, a computer system includes a single computer apparatus, where the subsystems can be the components of the computer apparatus. In other embodiments, a computer system can include multiple computer apparatuses, each being a subsystem, with internal components. Computer system 200 and any of its components or subsystems can include hardware and/or software elements configured as part of the systems and methods described herein.

Computer system 200 may include familiar computer components, such as one or more one or more data processors or central processing units (CPUs) 205, one or more graphics processors or graphical processing units (GPUs) 210, memory subsystem 215, storage subsystem 220, one or more input/output (I/O) interfaces 225, communications interface 230, or the like. Computer system 200 can include system bus 235 interconnecting the above components and providing functionality, such connectivity and inter-device communication.

The one or more data processors or central processing units (CPUs) 205 can execute logic or program code or for providing application-specific functionality. Some examples of CPU(s) 205 can include one or more microprocessors (e.g., single core and multi-core) or micro-controllers, one or more field-gate programmable arrays (FPGAs), and application-specific integrated circuits (ASICs). As user herein, a processor includes a multi-core processor on a same integrated chip, or multiple processing units on a single circuit board or networked.

The one or more graphics processor or graphical processing units (GPUs) 210 can execute logic or program code associated with graphics or for providing graphics-specific functionality. GPUs 210 may include any conventional graphics processing unit, such as those provided by conventional video cards. In various embodiments, GPUs 210 may include one or more vector or parallel processing units. These GPUs may be user programmable, and include hardware elements for encoding/decoding specific types of data (e.g., video data) or for accelerating 2D or 3D drawing operations, texturing operations, shading operations, or the like. The one or more graphics processors or graphical processing units (GPUs) 210 may include any number of registers, logic units, arithmetic units, caches, memory interfaces, or the like.

Memory subsystem 215 can store information, e.g., using machine-readable articles, information storage devices, or computer-readable storage media. Some examples can include random access memories (RAM), read-only-memories (ROMS), volatile memories, non-volatile memories, and other semiconductor memories. Memory subsystem 215 can include data and program code 240.

Storage subsystem 220 can also store information using machine-readable articles, information storage devices, or computer-readable storage media. Storage subsystem 220 may store information using storage media 245. Some examples of storage media 245 used by storage subsystem 220 can include floppy disks, hard disks, optical storage media such as CD-ROMS, DVDs and bar codes, removable storage devices, networked storage devices, or the like. In some embodiments, all or part of data and program code 240 may be stored using storage subsystem 220.

The one or more input/output (I/O) interfaces 225 can perform I/O operations. One or more input devices 250 and/or one or more output devices 255 may be communicatively coupled to the one or more I/O interfaces 225. The one or more input devices 250 can include the carriers as described above, cameras such as the electro-optical cameras described above, and can receive information from one or more sources for computer system 200. Some examples of the one or more input devices 250 may include a computer mouse, a trackball, a track pad, a joystick, a wireless remote, a drawing tablet, a voice command system, an eye tracking system, external storage systems, a monitor appropriately configured as a touch screen, a communications interface appropriately configured as a transceiver, or the like. In various embodiments, the one or more input devices 250 may allow a user of computer system 200 to interact with one or more non-graphical or graphical user interfaces to enter a comment, select objects, icons, text, user interface widgets, or other user interface elements that appear on a monitor/display device via a command, a click of a button, or the like.

The one or more output devices 255 can output information to one or more destinations for computer system 200. In the system of guidance of a surgical procedure disclosed above, the output devices may include a display device 9 as described above, or at least one of a display screen or monitor. The output devices 255 can include a communications interface appropriately configured as a transceiver, or the like. The one or more output devices 255 may allow a user of computer system 200 to view projected images of objects, icons, text, or other user interface elements. The one or more output devices 255 can include hardware and/or software elements configured for displaying information.

Communications interface 230 can perform communications operations, including sending and receiving data. Some examples of communications interface 230 may include a network communications interface (e.g. Ethernet, Wi-Fi, etc.). For example, communications interface 230 may be coupled to communications network/external bus 260, such as a computer network, a USB hub, or the like. A computer system can include a plurality of the same components or subsystems, e.g., connected together by communications interface 230 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Computer system 200 may also include one or more applications (e.g., software components or functions) to be executed by a processor to execute, perform, or otherwise implement techniques disclosed herein. These applications may be embodied as data and program code 240. Additionally, computer programs, executable computer code, human-readable source code, shader code, rendering engines, or the like, and data, such as image files, models including geometrical descriptions of objects, ordered geometric descriptions of objects, procedural descriptions of models, scene descriptor files, or the like, may be stored in memory subsystem 215 and/or storage subsystem 220.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

What is claimed is:

1. A system for guidance of a surgical procedure on a patient comprising:
   a computer comprising at least a processor and a memory;
   a display device communicatively linked with the computer;
   a mountable and movable electro-optical camera, wherein the camera, when mounted, has a known position and a known orientation relative to a surgeon performing the surgical procedure;
   a first carrier comprising at least 3 targets observable by the camera, wherein the first carrier is configured to be attached to a part of the patient;
   a second carrier comprising at least 3 targets observable by the camera concurrently with the at least 3 targets on the first carrier being observable by the camera, wherein the second carrier is configured to be attached to an implant that is to be attached to the part of the patient during the surgical procedure; and
   software, residing on the memory of the computer, comprising instructions that, when executed, cause the computer to:
      generate a three-dimensional (3D) digital representation of a pre-procedural geometry of the part of the patient;
      generate a 3D digital representation of a post-procedural geometry of the part of the patient that includes a representation of the implant; and
      calculate and display a projection of the 3D digital representation of the pre-procedural geometry of the part of the patient or the 3D digital representation of the post-procedural geometry of the part of the patient onto the display device in order for the displayed projection to match a view of the patient, wherein:
         the view is a current physical view of the patient by the surgeon; and
         the displayed projection is configured to show how the implant should be moved relative to the part of the patient to reach a desired position.

2. The system according to claim 1, wherein the 3D digital representation of the pre-procedural geometry of the part of the patient and the 3D digital representation of the post-procedural geometry of the part of the patient are adapted to be combined to a single digital representation.

3. The system of claim 1, wherein the camera is capable of capturing an image of the at least 3 targets on the first carrier and the at least 3 targets on the second carrier at the same instant.

4. The system of claim 1, wherein the displayed projection is configured to show how the implant should be moved relative to the part of the patient to reach the desired position and a desired orientation.

5. The system of claim 1, further comprising a third carrier comprising at least 3 targets observable by the camera, wherein the third carrier is configured to be mounted in a position and an orientation relative to any one of: (i) the part of the patient, (ii) the implant, or (iii) a surgical instrument.

6. The system of claim 1, wherein the camera is a digital camera calibrated to measure spatial directions to the targets of the first and second carriers in space.

7. The system of claim 1, wherein the targets are active light emitting elements.

8. The system of claim 1, wherein the camera is configured to be mounted to the head of the surgeon.

9. A system for guidance of a surgical procedure on a patient comprising:
   a head-mountable and movable digital camera, wherein the digital camera, when mounted, has a known position and a known orientation relative to a surgeon performing the surgical procedure;
   a first carrier comprising at least 3 light emitting elements observable by the digital camera, wherein the first carrier is configured to be attached to a part of the patient;
   a second carrier comprising at least 3 light emitting elements observable by the digital camera concurrently with the at least 3 light emitting elements on the first carrier being observable by the digital camera, wherein the second carrier is configured to be attached to an implant that is to be attached to the part of the patient during the surgical procedure, and wherein the second carrier is movable in relation to the first carrier during the surgical procedure;
   a display device configured to show how the implant should be moved; and
   a processor communicatively linked to the digital camera and the display device, wherein the processor is configured to perform operations including:
      generate a three-dimensional (3D) digital representation of a pre-procedural geometry of the part of the patient;
      generate a 3D digital representation of a post-procedural geometry of the part of the patient that includes a representation of the implant; and
      calculate and display a projection of the 3D digital representation of the pre-procedural geometry of the part of the patient or the 3D digital representation of the post-procedural geometry of the part of the patient onto the display device in order for the displayed projection to match a view of the patient;
   wherein the view is a current physical view of the patient by the surgeon;
   wherein the displayed projection is configured to show how the implant should be moved relative to the part of the patient to reach a desired position;
   wherein the 3D digital representation of the pre-procedural geometry of the part of the patient and the 3D digital representation of the post-procedural geometry of the part of the patient are adapted to be combined to a single digital representation;
   wherein the digital camera is capable of capturing an image of the at least 3 light emitting elements on the first carrier and the at least 3 light emitting elements on the second carrier at the same instant;
   wherein the displayed projection is configured to show how the implant should be moved relative to the part of the patient to reach the desired position and a desired orientation; and
   wherein the displayed projection is based on the image from the digital camera that includes the at least 3 light emitting elements of the first carrier and the at least 3 light emitting elements of the second carrier.

\* \* \* \* \*